United States Patent [19]

Closse et al.

[11] 4,252,817
[45] Feb. 24, 1981

[54] SUBSTITUTED-2,3-DIHYDROBENZOFURAN-2-ONES

[75] Inventors: Annemarie Closse, Binningen; Walter Haefliger, Basel; Daniel Hauser, Binningen, all of Switzerland

[73] Assignee: Sandoz Ltd., Basel, Switzerland

[21] Appl. No.: 37,717

[22] Filed: May 11, 1979

Related U.S. Application Data

[63] Continuation of Ser. No. 831,016, Sep. 6, 1977, abandoned, which is a continuation-in-part of Ser. No. 826,675, Aug. 22, 1977, abandoned, which is a continuation of Ser. No. 664,235, Mar. 5, 1976, abandoned.

[51] Int. Cl.³ .................. C07D 307/83; A61K 31/365
[52] U.S. Cl. .................................... 424/279; 562/469; 562/478; 424/317; 260/343.3 R
[58] Field of Search .................. 260/343.3 R; 424/279

[56] References Cited

U.S. PATENT DOCUMENTS

| | | | |
|---|---|---|---|
| 3,829,446 | 8/1974 | Kadin | 260/343.3 R |
| 3,993,665 | 11/1976 | Oediger et al. | 260/343.3 R |
| 4,013,690 | 3/1977 | Closse et al. | 260/343.3 R |
| 4,120,871 | 10/1978 | Gates et al. | 260/343.3 R |

OTHER PUBLICATIONS

Posternak et al., Helv. Chim. Acta., pp. 1564–1570, 1956.

Arora et al., Jour. Chem. Soc. Section C., p. 2865, 1971.
Kelly et al., Aust. Jour. Chem., 1969, 22, 977–991.

*Primary Examiner*—Henry R. Jiles
*Assistant Examiner*—Jane T. Fan
*Attorney, Agent, or Firm*—Gerald D. Sharkin; Robert S. Honor; Timothy G. Rothwell

[57] ABSTRACT

This invention provides new compounds of the formula,

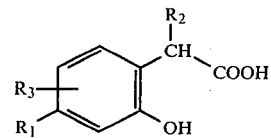

wherein
$R_1$ is alkyl of 1 to 10 carbon atoms, cycloalkyl of 3 to 8 carbon atoms or phenyl,
$R_2$ is hydrogen or lower alkyl, and
$R_3$ is halogen, nitro, lower alkyl, methylthio, hydroxy, lower alkoxy, acyloxy or acylamino; with the proviso that when $R_3$ is in the 5 position, and $R_1$ and $R_3$ are identical and signify a straight alkyl chain of 1 to 5 carbon atoms, $R_2$ is lower alkyl, useful as anti-phlogistics.

22 Claims, No Drawings

SUBSTITUTED-2,3-DIHYDROBENZOFURAN-2-ONES

This is a continuation, of application Ser. No. 831,016 filed Sept. 6, 1977, now abandoned, which in turn is a continuation-in-part of Ser. No. 826,675, filed Aug. 22, 1977, now abandoned, which in turn is a continuation of Ser. No. 664,235, filed Mar. 5, 1976, now abandoned.

The present invention relates to benzofuranone compounds.

In accordance with the invention there are provided new compounds of formula I,

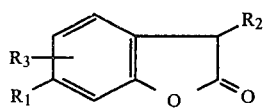

wherein $R_1$ is alkyl of 1 to 10 carbon atoms, cycloalkyl of 3 to 8 carbon atoms or phenyl, $R_2$ is hydrogen or lower alkyl, and $R_3$ is halogen, nitro, lower alkyl, methylthio, hydroxy, lower alkoxy, acyloxy or acylamino, with the proviso that when $R_3$ is in the 5 position and $R_1$ and $R_3$ are identical and signify a straight alkyl chain of 1 to 5 carbon atoms, $R_2$ is lower alkyl.

Further, in accordance with the invention a compound of formula I may be obtained by a process comprising lactonizing a compound of formula II,

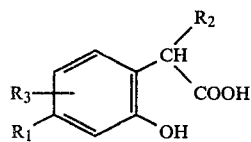

wherein $R_1$, $R_2$ and $R_3$ are as defined above.

A group of compounds suitably prepared by this process are compounds of formula I as defined above with the further proviso that when $R_1$ is alkyl of 1 to 5 carbon atoms and $R_3$ is halogen, alkyl or alkoxy, $R_2$ is lower alkyl.

When $R_1$ is cycloalkyl, this radical preferably signifies cyclopentyl or cycloheptyl, especially, however, cyclohexyl. When $R_1$ is alkyl, this preferably contains 3 to 6, especially 3 or 4 carbon atoms and is preferably branched and specially signifies isobutyl or isopropyl.

When $R_2$ is lower alkyl, this contains 1 to 4 carbon atoms and preferably signifies methyl.

The substituent $R_3$ preferably signifies halogen, i.e. chlorine, bromine or fluorine, and preferably signifies chlorine. When $R_3$ is lower alkyl or lower alkoxy, this preferably contains 1 to 4, especially 1 or 2 carbon atoms. When $R_3$ is an acyloxy or acylamino radical, this preferably contains 1 to 4, especially 2 carbon atoms. $R_3$ preferably is in the para-position to the hydroxy group.

In one group of compounds, $R_1$ is preferably cyclohexyl, phenyl or branched alkyl, $R_2$ is hydrogen or methyl and $R_3$ is chlorine or methyl.

The lactonization of compounds of formula II in accordance with the process of the invention is effected in accordance with conventional methods, as described in Example 1.

The compounds of formula II, also provided by this invention, used as starting materials, may be obtained in accordance with known methods, for example as described in the Examples or in manner analogous to the Examples. These compounds may be obtained in the usual manner from the corresponding compounds of formula II wherein $R_2$ and $R_3$ are hydrogen, and wherein the hydroxy group in the ring structure may optionally be protected temporarily by an alkoxy group, and the free carboxyl group may be protected temporarily by an ester group.

In the following non-limitative Examples all temperatures are indicated in degrees Centigrade and are uncorrected.

EXAMPLE 1

5-Chloro-6-cyclohexyl-2,3-dihydrobenzofuran-2-one 5 g of 5-chloro-4-cyclohexyl-2-hydroxyphenylacetic acid are dissolved in toluene with heating, 50 mg of p-toluenesulphonic acid are added, and the mixture is boiled in a water separator for 3 hours. The oil obtained after evaporation is purified on a 100-fold quantity of silica gel Merck. The desired product is eluted with chloroform and recrystallized from methylene chloride/petroleum ether. The crystals have an M.P. of 100°–102°.

The following compounds of formula I are produced in analogous manner, whereby $R_1$, $R_2$ and $R_3$ have the following significances:

| Example | $R_1$ | $R_2$ | $R_3$ | Melting point |
| --- | --- | --- | --- | --- |
| 2 | cyclohexyl | H | 5-Br | 124–126° |
| 3 | cyclohexyl | H | 7-Br | 108–109° |
| 4 | cyclohexyl | H | 5-NO$_2$ | 132–133° |
| 5 | cyclohexyl | CH$_3$ | 5-Cl | 92–93° |
| 6 | cyclohexyl | CH$_3$ | 5-NO$_2$ | 94–95° |
| 7 | phenyl | H | 5-Cl | 111–112° |
| 8 | cyclohexyl | H | 5-CH$_3$ | 157–158° |
| 9 | phenyl | CH$_3$ | 5-Cl | 88–89° |
| 10 | phenyl | H | 5-CH$_3$ | 77–78° |
| 11 | cyclohexyl | CH$_3$ | 5-OCH$_3$ | amorphous |
| 12 | cyclohexyl | H | 5-CH$_3$CONH | 195–196° |
| 13 | cyclohexyl | H | 5-CH$_3$S | 104–105° |
| 14 | (CH$_3$)$_2$CHCH$_2$– | H | 5-Cl | 28–29° |

| Example | R₁ | R₂ | R₃ | Melting point |
|---------|-----|-----|---------|-----------|
| 15 |  | H | 5-OH | amorphous |
| 16 |  | H | 5-CH₃COO | amorphous |

EXAMPLE 17

4-Cyclohexyl-2-hydroxy-5-nitrophenylacetic acid 1.06 ml of 100% nitric acid are slowly added dropwise at −10° to a solution of 5.9 g of 4-cyclohexyl-2-hydroxy-phenylacetic acid in 100 ml of absolute methylene chloride. The mixture is finally stirred for 10 minutes without further cooling, the methylene chloride solution washed several times with water, dried over sodium sulphate and evaporated to yield the title compound.

NMR Spectrum (DMSO): 1.0–2.1 (10H); 3.1 b (1H); 3.53 s (2H); 6.88 (1H); 7.77 (1H).

EXAMPLE 18

5- and 3-Bromo-4-cyclohexyl-2-hydroxy-phenylacetic acid 7.0 g of 4-cyclohexyl-2-hydroxy-phenylacetic acid, 5.34 g of N-bromosuccinimide and 6.0 g of succinimide are suspended in 500 ml of dry methylene chloride and stirred for 5 days at room temperature. The methylene chloride solution is washed several times with water, dried and evaporated. The yellow, oily residue is fractionally crystallized from ether/petroleum ether. The first fraction of crystals contains 3-bromo-4-cyclohexyl-2-hydroxy-phenylacetic acid.

NMR Spectrum (DMSO): 2.9 b (1H); 4.0 s (2H); 7.15+7.35 AB (J=8 Hz).

The third fraction of crystals contains 5-bromo-4-cyclohexyl-2-hydroxy-phenylacetic acid.

NMR Spectrum (DMSO): 2.85 b (1H); 3.47 s (2H); 6.85 s (1H); 7.37 s (1H).

EXAMPLE 19

5-Chloro-4-cyclohexyl-2-hydroxyphenylacetic acid 3.54 g of N-chlorosuccinimide and 5.25 g of succinimide are added to a solution of 6.2 g of 4-cyclohexyl-2-hydroxy-phenylacetic acid in 200 ml of dry methylene chloride and the mixture left to react for 5 days at room temperature. The clear reaction solution is washed twice with 1 N hydrochloric acid and once with water, dried and evaporated. The white crystalline residue can either be worked up directly or purified by recrystallization from methylene chloride/petroleum ether.

NMR Spectrum (CDCl₃): 1.0–2.0 b (10H); 2.90 m (1H); 3.60 s (2H); 6.75 s (1H); 7.07 s (1H); 8.7 b (2H).

EXAMPLE 20

5-Hydroxy-2-methyl-4-biphenylacetic acid (a) 2-Formyl-5-methxoy-4-biphenylacetic acid 24.3 g of 3-methoxy-4-biphenylacetic acid are dissolved in 400 ml of methylene chloride and 22 ml of titanium chloride added at 0° whilst stirring. 8.65 ml of 1,1-Dichloromethylmethyl ether are added over a period of 30 minutes and the mixture finally stirred for one hour at 20°. The reaction mixture is worked up by pouring onto 500 ml of ice/water and the phases separated using a separating funnel. The aqueous layer is extracted three times with ethyl acetate. The organic phases are washed with water, dried over Na₂SO₄ and concentrated. The residue is evaporated with 200 ml of toluene.

The raw product is recrystallized from methylene chloride/hexane to give 2-formyl-5-methoxy-4-biphenylacetic acid. M. pt. 174°–175°.

(b) 5-Methoxy-2-methyl-4-biphenylacetic acid 4 g of 2-Formyl-5-methoxy-4-biphenylacetic acid are dissolved in 300 ml of dry tetrahydrofuran and 2.5 g of sodium borohydride added. The reaction mixture is warmed to 80° for 40 minutes and, after cooling, dropped onto 150 g of ice, acidified with 2 N hydrochloric acid and extracted three times with ethyl acetate. The organic phases are washed with saturated brine, dried over Na₂SO₄ and concentrated. The residue is hydrogenated in 200 ml of ethyl acetate in the presence of 250 mg of Pd (10% on active charcoal) at a hydrogen pressure of 2 atmospheres. After three hours, the reaction mixture is filtered through talc and the filtrate evaporated. The product is recrystallized from ethyl acetate. M. pt. 127°–128°.

(c) 5-Hydroxy-2-methyl-4-biphenylacetic acid 2 g of 5-Methoxy-2-methyl-biphenylacetic acid are dissolved in 250 ml of dry methylene chloride and 2 ml of boron tribromide added dropwise at 0°. After 60 minutes, the reaction mixture is dropped, with cooling and stirring, onto 250 ml of ice/water and the mixture separated using a separating funnel. The aqueous layer is extracted three times with ethyl acetate. The organic phases are washed twice with water, dried over Na₂SO₄ and evaporated. The residue comprises raw 5-hydroxy-2-methyl-4-biphenylacetic acid.

The following compounds can be prepared in manner analogous to Examples 17 to 20, using appropriate starting materials in approximately equivalent amounts.

EXAMPLE 21

5-Chloro-4-cyclohexyl-2-hydroxy-α-methyl-phenylacetic acid

NMR Spectrum (CDCl₃): 1.0–2.1 (13H); 2.9 m (1H); 3.86 q (J=7; 1H); 6.75 (1H); 7.1 (3H).

EXAMPLE 22

4-Cyclohexyl-2-hydroxy-α-methyl-5-nitrophenylacetic acid

NMR Spectrum (DMSO): 1.0–2.1 (13H); 3.15 b (1H); 3.9 q (J=7; 1H); 6.92 (1H); 7.71 (1H).

EXAMPLE 23

2-Chloro-5-hydroxy-4-biphenylacetic acid M. pt. (lactone): 111°–112°.

EXAMPLE 24

4-Cyclohexyl-2-hydroxy-5-methylphenylacetic acid

M. pt. (lactone): 157°–158°.

EXAMPLE 25

2-(2-Chloro-5-hydroxy-4-biphenyl)-propionic acid

M. pt. (lactone): 88°–89°.

EXAMPLE 26

5-Chloro-2-hydroxy-4-isobutylphenylacetic acid

NMR Spectrum (DMSO): 0.8–1.1 (6H); 1.86 m (1H); 2.48 d (J=7 Hz; 2H); 3.43 s (2H); 6.68 (1H); 7.12 (1H).

EXAMPLE 27

Tablets containing 30 mg of the active agent

|  | mg |
|---|---|
| 5-Chloro-4-cyclohexyl-2-hydroxy-phenylacetic acid | 30 |
| Magnesium stearate | 0.6 |
| Polyvinylpyrrolidone | 6 |
| Corn starch | 14 |
| Lactose (pulv) | 87.4 |
| Cellulose (microcrystalline) | 2 |
|  | 140 |

EXAMPLE 28

Dragees containing 30 mg of the active agent

Dragee kernels can be prepared from the adjuvants of Example 27 in known manner and coated according to known methods to produce dragees.

EXAMPLE 29

Capsules containing 50 mg of the active agent

|  | mg |
|---|---|
| 5-Chloro-4-cyclohexyl-2-hydroxy-phenylacetic acid | 50 |
| Lactose (pulv.) | 134.5 |
| Corn starch | 111 |
| Silicic acid (highly dispersed) | 1.5 |
| Magnesium stearate | 3.0 |
| For a capsule content of | 300 |

The materials are mixed together, the mixture sieved and filled into capsules.

The compounds of formulae I and II are useful because they exhibit pharmacological activity. In particular they exhibit oedema and inflammation inhibitory, as well as anti-arthritic, activity as indicated in standard tests, e.g. the carrageen paw oedema test, the adjuvans arthritis test, the sub-chronic granuloma cyst test in the rat and in the U.V. erythema test in the guinea pig. Satisfactory results are obtained in these tests on administration p.o. of from about 0.5 to about 10 mg/kg animal body weight of the compounds. The compounds exhibit an activity spectrum similar to known non-steroidal anti-phlogistic agents, such as Indomethazin and Phenylbutazone. The compounds also similarly exhibit an anti-pyretic effect, e.g. in the yeast fever rat, and an analgesic effect. The compounds also similarly inhibit in vitro P.G. synthetase and Collagen induced blood platelet aggregation.

The compounds are therefore useful as anti-phlogistics as well as anti-arthritics, analgesics, anti-pyretics and blood platelet aggregation inhibitors.

For the above mentioned use the dosage will, of course, vary depending on the compound employed, mode of administration and therapy desired. However, in general, satisfactory results are obtained when administered at a daily dosage of from 0.5 to about 10 mg per kg animal body weight, conveniently given in divided doses 2 to 4 times a day or in sustained release form.

For the larger mammal, the total daily dosage is in the range from about 20 to 3000 mg, preferably from about 60 to about 300 mg, and dosage forms suitable for oral administration comprise from about 15 mg to about 150 mg of the compounds admixed with a solid or liquid pharmaceutical carrier or diluent.

The compounds of formula II possess particularly advantageous properties.

The Example 1, 7 and 21 compounds exhibit especially interesting activity.

The compounds of formula II may exist in salt form. The free acids may be converted into salt forms in known manner and vice versa. Examples of salts with inorganic bases are, for example, alkali metal salts such as sodium or potassium salts or alkaline earth metal salts such as calcium salts. Examples of organic bases suitable for salt formation include amines.

The present invention also provides a pharmaceutical composition comprising a compound of formula II in free acid or salt form, in association with a pharmaceutical carrier or diluent. Such compositions may be in the form of, for example, a solution or a tablet.

Conveniently there are provided compounds of formula I, wherein $R_1$ is alkyl of 1 to 5 carbon atoms, $R_2$ is hydrogen, and $R_3$ is halogen, lower alkyl or lower alkoxy, in the form of a pharmaceutical composition.

The aforementioned preferred substituents also refer to the compounds of formula II.

What is claimed is:

1. A compound of the formula

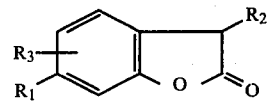

wherein
   $R_1$ is cycloalkyl having 3 to 8 carbon atoms or phenyl, and
   $R_2$ is hydrogen or lower alkyl, and
   $R_3$ is halogen, nitro, methylthio, hydroxy, lower alkoxy, lower alkanoyloxy having 1 to 4 carbon atoms or lower alkanoylamino having 1 to 4 carbon atoms.

2. A compound of the formula

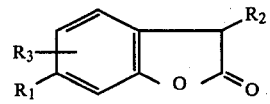

wherein
   $R_1$ is cycloalkyl having 3 to 8 carbon atoms or phenyl, and
   $R_2$ is hydrogen or lower alkyl, and
   $R_3$ is chlorine, bromine, fluroine, or lower alkoxy.

3. The compound of claim 1 wherein $R_1$ is cyclohexyl.

4. The compound of claim 1 wherein $R_1$ is phenyl.

5. The compound of claim 1 wherein $R_3$ is chlorine.

6. The compound of claim 1 wherein $R_1$ is cyclohexyl, $R_2$ is hydrogen and $R_3$ is chlorine, bromine or fluorine.

7. The compound of claim 1 which is 5-chloro-6-cyclohexyl-2,3-dihydrobenzofuran-2-one.

8. The compound of claim 1 which is 5-chloro-6-phenyl-2,3-dihydrobenzofuran-2-one.

9. The compound of claim 1 wherein $R_1$ is cycloalkyl having 3 to 8 carbon atoms.

10. The compound of claim 3 wherein $R_2$ is hydrogen and $R_3$ is 5-bromo.

11. The compound of claim 3 wherein $R_2$ is hydrogen and $R_3$ is 7-bromo.

12. The compound of claim 3 wherein $R_2$ is hydrogen and $R_3$ is 5-nitro.

13. The compound of claim 3 wherein $R_2$ is methyl and $R_3$ is 5-chloro.

14. The compound of claim 3 wherein $R_2$ is methyl and $R_3$ is 5-nitro.

15. The compound of claim 4 wherein $R_2$ is methyl and $R_3$ is 5-chloro.

16. The compound of claim 3 wherein $R_2$ is methyl and $R_3$ is 5-methoxy.

17. The compound of claim 3 wherein $R_2$ is hydrogen and $R_3$ is 5-acetamido.

18. The compound of claim 3 wherein $R_2$ is hydrogen and $R_3$ is 5-methylthio.

19. The compound of claim 4 wherein $R_2$ is hydrogen and $R_3$ is 5-OH.

20. The compound of claim 4 wherein $R_2$ is hydrogen and $R_3$ is 5-acetyloxy.

21. A pharmaceutical composition for use in treating oedemas, inflammations and arthritis which comprises an effective amount of a compound of claim 1 in association with a pharmaceutically acceptable carrier or diluent.

22. A method of treating oedemas, inflammations and arthritis in animals which comprises administering a therapeutically effective amount of a compound of claim 1 to an animal in need of such treatment.

* * * * *

UNITED STATES PATENT AND TRADEMARK OFFICE
CERTIFICATE OF CORRECTION

PATENT NO. : 4,252,817

DATED : February 24, 1981

INVENTOR(S) : Closse et al.

It is certified that error appears in the above-identified patent and that said Letters Patent is hereby corrected as shown below:

Title page, left-hand column; directly beneath the last line of the cross-reference under the heading "Related U.S. Application Data", please insert the heading entitled --Foreign Application Priority Data-- and insert directly beneath the new heading --Sept. 8, 1976[CH] Switzerland     11386/76

Sept. 10, 1976[CH] Switzerland    11529/76

March 12, 1975[CH] Switzerland    3129/75

July 24, 1975[CH] Switzerland     9678/75 --

Signed and Sealed this

Fourth Day of January 1983

[SEAL]

Attest:

Attesting Officer

GERALD J. MOSSINGHOFF

Commissioner of Patents and Trademarks